United States Patent
Case et al.

(10) Patent No.: US 7,272,434 B2
(45) Date of Patent: Sep. 18, 2007

(54) AUTOMATIC POST-PACING INTERVAL MEASUREMENT

(75) Inventors: Jason A. Case, San Jose, CA (US); Thomas J. Holly, San Jose, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 202 days.

(21) Appl. No.: 10/917,683

(22) Filed: Aug. 13, 2004

(65) Prior Publication Data

US 2006/0036291 A1    Feb. 16, 2006

(51) Int. Cl.
*A61B 5/0428* (2006.01)

(52) U.S. Cl. .................................................. 600/510

(58) Field of Classification Search ............... 600/510, 600/515, 518, 522; 128/901, 902
See application file for complete search history.

(56) References Cited

U.S. PATENT DOCUMENTS

| | | | |
|---|---|---|---|
| 4,248,244 A | 2/1981 | Charnitski et al. |
| 4,905,708 A | 3/1990 | Davies |
| 5,503,160 A | 4/1996 | Pering et al. |
| 5,601,088 A | 2/1997 | Swanson et al. |
| 5,605,157 A | 2/1997 | Panescu et al. |
| 5,694,943 A | 12/1997 | Brewer et al. |
| 5,813,991 A | 9/1998 | Willis et al. |
| 5,876,350 A | 3/1999 | Lo et al. |
| 6,029,087 A | 2/2000 | Wohlgemuth |
| 6,077,236 A | 6/2000 | Cunningham |
| 6,088,614 A | 7/2000 | Swanson |
| 6,185,450 B1 | 2/2001 | Seguine et al. |
| 6,236,883 B1 | 5/2001 | Ciaccio et al. |
| 6,304,772 B1 | 10/2001 | Taha et al. |
| 6,360,126 B1 | 3/2002 | Mika et al. |
| 6,591,131 B2 | 7/2003 | Dal-Molin |
| 2004/0064059 A1 | 4/2004 | Samuelson et al. |

FOREIGN PATENT DOCUMENTS

| | | |
|---|---|---|
| EP | 1 512 431 A1 | 3/2005 |
| WO | WO 2006/017858 A1 | 2/2006 |

OTHER PUBLICATIONS

Cooper DH. Kennedy HL. Lyyski DS. Sprague MK. Holter triage ambulatory ECG analysis: Accuracy and time efficiency. Journal of Electrocardiology. vol. 29(1)(pp. 33-38), 1996.

Shaw, G.R.; Savard, P. On the detection of QRS variations in the ECG. Biomedical Engineering, IEEE Transactions on, vol. 42, No. 7, pp. 736-741, Jul. 1995.

(Continued)

*Primary Examiner*—Carl Layno
*Assistant Examiner*—Yun Haeng Lee
(74) *Attorney, Agent, or Firm*—Vista IP Law Group LLP

(57) ABSTRACT

A method for processing a biopotential signal includes detecting a pacing signal, and applying a dynamic filter on a pacing channel based on the detected pacing signal. A method for processing a biopotential signal includes detecting a pacing signal, and automatically obtaining a post-pacing interval based at least in part on the pacing signal.

39 Claims, 7 Drawing Sheets

OTHER PUBLICATIONS

Stevenson WG. Sager PT, Friedman PL. Entrainment techniques for mapping atrial and ventricular tachycardias. Journal of Cardiovascular Electrophysiology. vol. 6(3)(pp. 201-216), 1995.

Klitzner, Thomas S., et al., "Effects of Filtering on Right Ventricular Electrograms Recorded from Endocardial Cathethers in Human," PACE, vol. 13, pp. 69-77 (Jan. 1990).

PCT International Search Report for PCT/US2005/028926, Applicant: Boston Scientific Scimend, Inc., Form PCT/ISA/210 and 220, dated Jan. 25, 2006 (7 pages).

PCT Written Opinion of the International Search Authority for PCT/US2005/028926, Applicant: Boston Scientific Scimend, Inc., Form PCT/ISA/237, dated Jan. 25, 2006 (6 pages).

AUTOMATIC POST-PACING INTERVAL MEASUREMENT

FIELD OF THE INVENTION

The present invention relates generally to tissue characterization for identification of an ablation site, and more particularly, to apparatuses and methods for obtaining post-pacing interval measurement.

BACKGROUND OF THE INVENTION

A normal heartbeat involves generation of an electrical impulse and propagation of the electrical impulse across the heart, which causes each chamber of the heart to appropriately contract. Sometimes aberrant conductive pathways develop in heart tissues, and disrupt the normal path of the electrical impulse. For example, anatomical obstacles or conduction blocks in heart tissue can disrupt the normal propagation of an impulse by causing the impulse to degenerate into several circular wavelets that circulate about the obstacles, thus disrupting normal activation within the heart tissue and chambers. Also, slow conduction zones in animal and human hearts constrained by anatomical or conduction blocks are believed to exist. Such a zone is a localized region of the heart tissue which propagates an impulse at a slower speed than normal heart tissue thus sometimes resulting in errant, circular propagation patterns or reentrant pathways. Reentrant pathways provide the substrates for the re-excitation of a region of cardiac tissue by an excitatory wavefront. Reentry may continue for one or more cycles and may sometimes result in tachycardia. Reentrant ventricular tachycardia (VT) is an abnormally rapid ventricular rhythm with aberrant ventricular excitation (wide QRS complexes), usually in excess of 150 per minute, which is generated within the ventricle of the heart as a result of a reentrant pathway.

To treat VT, it is desirable first to determine the physical location of the aberrant pathways. Once located, the heart tissue in the pathway can be ablated and destroyed by heat, chemicals, and/or other means. Heat can be generated in the targeted tissue using, for example, radio frequency (RF) energy, microwave energy, ultrasonic energy, or lasers to effect the ablation lesion. Ablation can remove the aberrant conductive pathway, restoring normal myocardial contraction. More specifically, to treat VT, the targeted conduction zone must be located and destroyed (or partially destroyed), with the goal of eliminating the conduction zone's ability to conduct electrical impulses.

In order to determine the physical location of the aberrant pathways, physicians have performed entrainment mapping. For example, entrainment mapping of re-entrant tachycardia is often used for identifying critical pathways of aberrant intracardiac conduction. Concealed entrainment of an arrhythmia requires that a post-pacing interval (PPI) be obtained. For example, in one protocol, concealed entrainment of an arrhythmia requires, among other criteria, that a PPI be within approximately 20 ms of a tachycardia cycle length. However, existing devices do not allow PPI measurements be obtained efficiently and conveniently. Particularly, when a pacing signal is routed to a biopotential sensing catheter that is connected to a diagnostic recording system, the biopotential recordings from the catheter can be obscured. This can be the result of the differential between the pacing signal (e.g., generally in the range of tens of volts) and an intracardiac biopotential (e.g., generally in the range of several millivolts). Recording amplifiers' responses to large transient spikes (e.g., step response of a signal processing chain) can also cause a variety of phenomenon, such as, saturation, overshooting, ringing, that can obscure biopotential recordings. As a result, a user may be required to manually manipulate existing software and manually process data in order to obtain a desired information associated with a particular biopotential recording.

Furthermore, existing software may automatically clip off valuable data associated with signal on a pacing channel, thereby making it difficult for a user to obtain desired information from a diagnostic recording. FIG. 1 illustrates an example of a display window 100 displaying data 102 that are generated using existing systems. Data 104 (shown in dotted-line) beyond the display window 100, including valuable biopotential data 106, are being clipped off by existing software because they are out of range. In such cases, in order to obtain a PPI, a user may need to modify existing software to search for the biopotential data 106. After the biopotential data 106 is located, the user may then need to manually measure or calculate a duration between a pace signal and the biopotential data 106 to obtain the PPI. This lengthens the amount of time necessary to diagnose a patient, and can complicate a diagnostic procedure.

Thus, there is currently a need for an improved device and method for obtaining biopotential data, and more specifically, for obtaining a post-pacing interval.

SUMMARY OF THE EMBODIMENTS

In accordance with some embodiments of the invention, a system for processing a biopotential signal includes a detector for detecting a pacing signal, and a filtering module for applying a dynamic filter based on the detected pacing signal.

In accordance with other embodiments of the invention, a method for processing a biopotential signal includes detecting a pacing signal, and applying a dynamic filter on a pacing channel based on the detected pacing signal.

In accordance with other embodiments of the invention, a computer software product having a set of stored instructions, an execution of which causes a process to be performed, the process comprising detecting a pacing signal, and applying a dynamic filter on a pacing channel based on a detected pacing signal.

In accordance with other embodiments of the invention, a system for processing a biopotential signal includes a detector for detecting a pacing signal, and means for automatically obtaining a post-pacing interval based at least in part on the pacing signal.

In accordance with other embodiments of the invention, a method for processing a biopotential signal includes detecting a pacing signal, and automatically obtaining a post-pacing interval based at least in part on the pacing signal.

In accordance with other embodiments of the invention, a computer software product having a set of stored instructions, an execution of which causes a process to be performed, the process comprising detecting a pacing signal, and automatically obtaining a post-pacing interval based at least in part on the pacing signal.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention. It should be noted that the figures are not drawn to scale and that elements of similar structures or functions are represented by like reference numerals throughout the figures. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
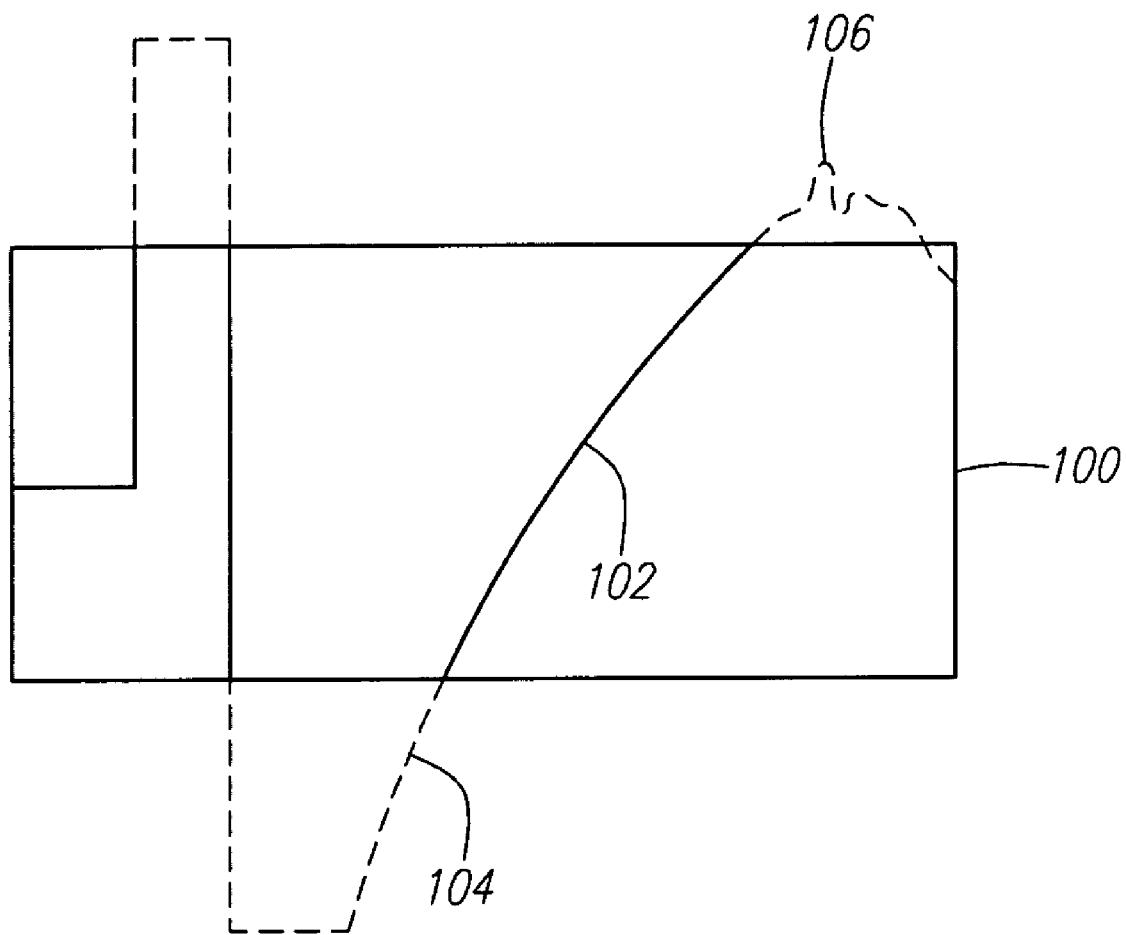
FIG. 1 is an example of an electrogram, particularly showing biopotential data being clipped off.

Various embodiments of the present invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an aspect described in conjunction with a particular embodiment of the present invention is not necessarily limited to that embodiment and can be practiced in any other embodiments of the present invention.

Figure 2:
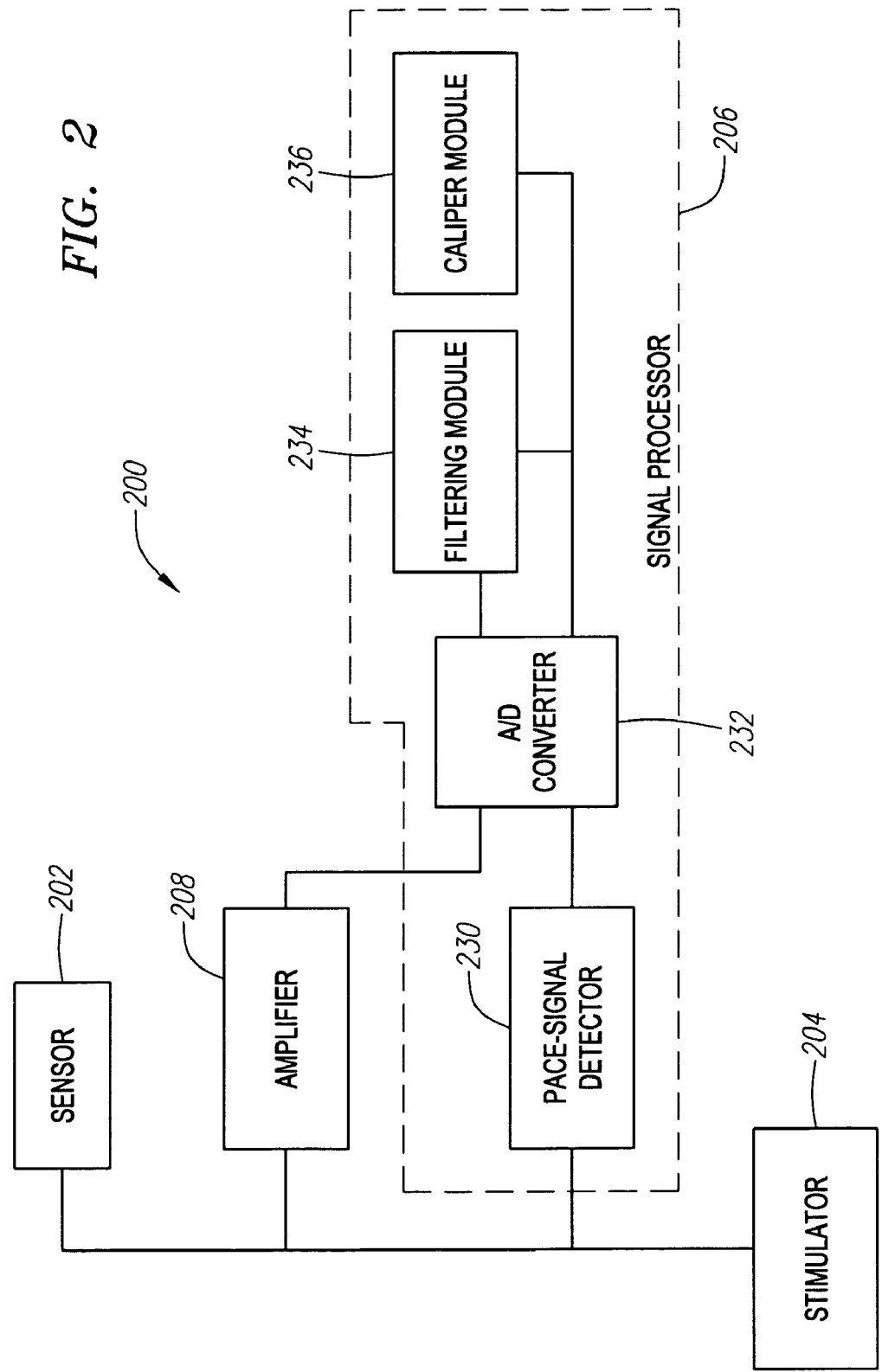
FIG. 2 is a block diagram of a system for sensing biopotentials in accordance with some embodiments of the invention.

FIG. 2 illustrates a mapping system 200 in accordance with embodiments of the invention. The mapping system 200 includes a sensor 202 for sensing cardiac signals (e.g., biopotentials), a stimulator 204 for generating pacing signals, and a signal processor 206 coupled to the sensor 202 and the stimulator 204. The sensor 202 can be a monopolar sensor or a bipolar sensor, and is carried on a structure (not shown), such as a catheter, a probe, or an expandable device (e.g., a basket or a balloon). In other embodiments, the system 200 can include more than one sensor. In the illustrated embodiments, the stimulator 204 is configured to generate pace signals at a rate that is faster than a cycle of a cardiac signal. For example, if a cardiac signal cycle is 250 milliseconds (ms), the stimulator 204 can be configured to generate a pace signal every 240 ms, thereby allowing a cardiac signal to be "captured". In some embodiments, the stimulator 204 can be integrated with the sensor 202, in which cases, the sensor 202 can be used to emit pace signals and sense biopotentials. The signal processor 206 is configured to receive a sensed cardiac signal from the sensor 202 and a pace signal from the stimulator 204, and generate a feedback based at least in part on the received cardiac signal and the pace signal. The signal processor 206 will be described in further detail below.

In the illustrated embodiments, the mapping system 200 further includes an amplifier 208 for amplifying sensed cardiac signals before they are transmitted to the signal processor 206. In some embodiments, the amplifier 208 can be implemented as a component of a recorder, which records or temporarily save biopotential signals for later use. In alternative embodiments, the amplifier 208 can be implemented as a component of the catheter. In further embodiments, the amplifier 208 is optional, and the system 200 does not include the amplifier 208.

The signal processor 206 includes a pace-signal detector 230 for detecting a pace signal generated by the stimulator 204, an analog-to-digital (A/D) converter 232 for converting signals into digital format, a filtering module 234, and a caliper module 236. In other embodiments, the pace-signal detector 230 can be implemented as a component of the stimulator 202, in which case, the signal processor 206 does not include the pace-signal detector 230. Also, in other embodiments, signals received from the sensor 202 are already in digital format, in which cases, the A/D converter 232 is configured to convert pace signals into digital format, and sensed cardiac signals are passed directly from the pace-signal detector 230 to the filtering module 234. Alternatively, signals received from the stimulator 204 are already in digital format, in which case, the A/D converter 232 is configured to convert sensed cardiac signals into digital format, and detected pace signals are passed directly from the amplifier 208 to the filtering module 234. In further embodiments, signals received from both the sensor 202 and from the stimulator 204 are already in digital format, in which case, the signal processor 206 does not include the A/D converter 232, and signals received from the sensor 202 and the stimulator 204 are passed directly to the filtering module 234.

The filtering module 234 is configured to apply a dynamic filter to eliminate any baseline shift of a pace channel that could obscure post-pacing signal recovery, while preserving low frequency signal content in a recorded biopotential. In the illustrated embodiments, the filtering module 234 is configured to apply a high pass filter having a first 3DB point value. When the pace-signal detector 230 detects a pace signal, the filtering module 234 toggles the first 3DB point value to a second 3DB point value, and maintain the high pass filter at the second 3DB point value for a prescribed duration dT. After the prescribed duration dT has lapsed, the dynamic filter is then toggled back from the second 3DB point value to the first 3DB point value. The prescribed duration dT can be, for example, any value that is between approximately 10 milliseconds (ms) and 100 ms, and more preferably, between approximately 10 ms and approximately 50 ms. However, the prescribed duration dT can be a different value in alternative embodiments, depending on the particular application.

As used in this specification, the term "3DB point value" refers to a characterization of a filter's frequency response. For example, a unity gain high pass filter having a 3DB point value of 30 Hertz (i.e., a 30 Hertz high pass filter) will have a gain of 0.707 at 30 Hz. As such, a signal having a frequency that is higher than 30 Hertz will have a corresponding gain that is higher than 0.707, while a signal having a frequency that is lower than 30 Hertz will have a corresponding gain that is lower than 0.707. In the illustrated embodiments, the first 3DB point value can be a value that is between approximately 0.5 hertz (Hz) and 50 Hz, and more preferably, between approximately 20 Hz and 40 Hz (e.g., 30 Hz), and the second 3DB point value can be a value that is between approximately 80 Hz and 120 Hz, and more preferably, between 90 Hz and 110 Hz (e.g., 100 Hz). In other embodiments, the first 3DB point value can be zero. In further embodiments, the filtering module 234 can be configured to toggle the filter between a first 3DB point value and a second 3DB point value that are different from the values described previously.

Toggling the dynamic high pass filter from the first 3DB point value to the second 3DB point value provides a better step response, and toggling the dynamic high pass filter back to the first 3DB point value allows a full bandwidth of biosignal be captured after obtaining the better step response.

In the illustrated embodiments, the filtering module 234 is configured to toggle the dynamic high pass filter from a first 3DB point value to a second 3DB point value at every detected pace signal. Alternatively, a user interface can be provided that allows a user to control the filtering module 234 such that the filter is toggled from the first 3DB point value to the second 3DB point value for the prescribed duration for a detected pace signal selected by the user. In some embodiments, the signal processor 206 also includes a user interface (e.g., a button or a control) which allows a user to select the first value, the second value, and/or the duration dT. Alternatively, the first 3DB point value, the second 3DB point value, and/or the duration dT can be default values set by a manufacturer of the signal processor 206. The filtering module 234 can be implemented using software, hardware, or a combination of software and hardware, using techniques known in the art.

In other embodiments, the filtering module 234 can be configured to apply a median filter to the response signals. With a median filter, the boxcar width is less than half the width of the narrowest expected electrogram. In a preferred embodiment, the width is between 10 ms and 20 ms. Applying a median filter distorts the shape of the waveform of an electrogram, but leaves the width of the electrogram unmodified.

In further embodiments, the filtering module 234 can be configured to apply a low-pass filter to the response signals. Low-pass filtering provides several benefits. This filtering process tends to decrease the effects of noise and removes near-zero values. The median filter is relatively tolerant to such low values. Electrogram durations will be biased to lower numbers without the low-pass filters. Also, if the median filter is chosen to be quite narrow, e.g. 5 ms, electrogram duration can be measured to be much shorter than it would be if measured manually by an expert electrophysiologist. Conventional low-pass filtering tends to widen the processed signal. Therefore, if a box-car averaging method is used, the measured duration of the processed signal needs to be decreased by the width of the boxcar used for filtering. Various other low-pass filtering procedures may be used. For a given filter, however, the duration measured generally needs to be adjusted downward by the width of the filter's impulse response.

In general, any filtering performed by the filtering module 234 can be accomplished by an appropriately programmed computer/processor or dedicated hardware designed to perform one or more signal processing/filtering functions.

Figure 3:
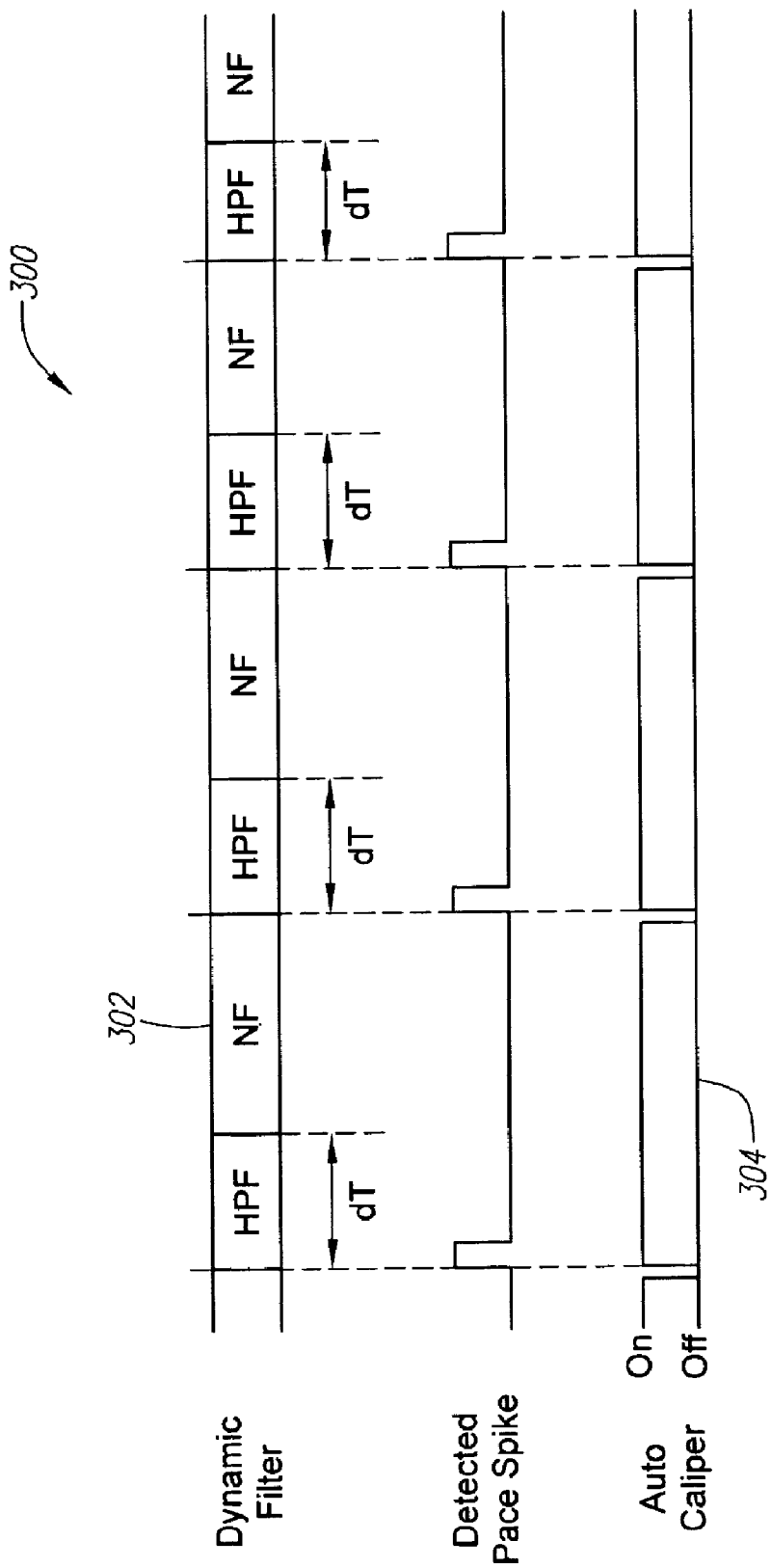
FIGS. 3 and 4 illustrate logics of a filtering module and a caliper module in accordance with some embodiments of the invention.
Figure 4:
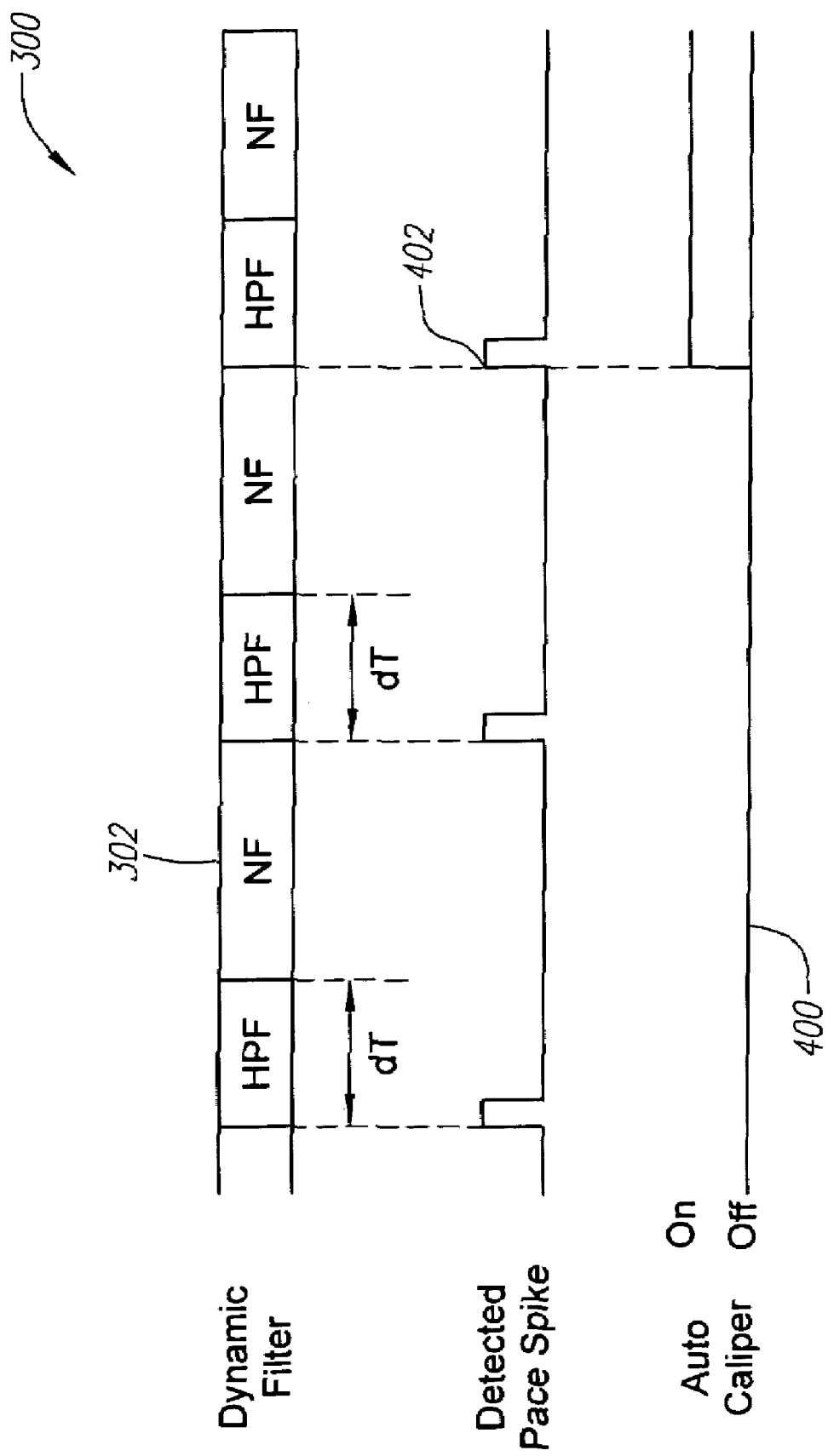

In the illustrated embodiments, when a pace signal is detected by the pace-signal detector 230, the caliper module 236 is also activated to measure a duration between the detected pace signal and a next detected biopotential, thereby obtaining a post-pacing interval (PPI). FIGS. 3 and 4 illustrate logics 300 of the filtering module 234 and the caliper module 236 in accordance with embodiments of the invention. As shown in FIGS. 3 and 4, the filtering module 234 is configured to toggle a dynamic filter between a first 3DB point (e.g., 30 Hz) to a second 3DB point (e.g., a 100 Hz) for a prescribed duration dT when a pace signal is detected (See filter timing graphs 302). If the filtering module 234 is configured to toggle the dynamic filter every time when a pace signal is detected, the caliper module 236 can be configured to obtain a PPI value for every detected pace signal (See caliper timing graph 304 in FIG. 3). Alternatively, a physician can use the interface described previously to select a detected pace signal as a reference 402, based on which, the caliper module 236 will obtain a PPI value. In such case, the caliper module 236 is activated to obtain the PPI associated with the selected pace signal (See caliper timing graph 400 in FIG. 4B). Using the caliper module 236 to automatically obtain PPI value(s) is advantageous because it obviates the need for a physician to manually manipulate software and/or data to obtain the PPI value(s), which can be time consuming and subjected to human errors.

In order for the caliper module 236 to automatically determine post-pacing intervals, electrogram complexes need to be identified in a recording channel before measuring or estimating response signal interval. Automatic detection of biological signal complexes with short durations and fast repetition rates has been studied and reported in both scientific publications and in patent disclosures. Also, signal processing of electrograms including ECGs (electrocardiograms), EEGs, and other biological signals generally is well-known. Two publications describing automatic detection of the ECG waveform are: (1) "Holter triage ambulatory ECG analysis: Accuracy and time efficiency," Cooper et al., J Electrocardiol., 1(1), pp. 33-38, 1996; and (2) "On the detection of QRS variations in the ECG," Shaw et al., IEEE Trans BiomedEng., 42(7), pp. 736-741, 1995.

In general, all electrogram complexes have multiple peaks and zero crossings. A duration of a signal or an electrogram is defined herein to mean the time from the first "significant" deviation from the recording baseline to time at which no further "significant" deviation is observed. This definition of electrogram duration results in a non-stationary value for duration as noise is added to the system. That is, the duration becomes shorter as the signal is corrupted by more noise. For normal electrogram recordings, noise is small compared to the electrogram signal, resulting in duration determinations very close to those that would be obtained in a noise-free environment. For fractionated electrograms which may result from a slow conduction zone, however, noise can be significant. Therefore, signals with as low a noise level as possible is sought, and signal processing is applied to reduce the effects of noise in accordance with embodiments of the invention. In some embodiments, all signals with values above a threshold level are considered significant and become a part of an electrogram complex. One method of finding the beginning and end of the complex is to search backward and forward from the peak of the processed signal to find the first occurrences of signals below the threshold to find the beginning and end of the complex, respectively.

The threshold can be defined in various ways. In one embodiment, the threshold is defined in terms of percentage of the peak electrogram amplitude. In another embodiment, the threshold is defined as a fixed signal amplitude, such as 0.1 millivolt (mV). In a preferred embodiment, the threshold is defined as a value based on characteristics of the signal being recorded, i.e., an adaptive threshold. An adaptive threshold value may be the median value of all processed signal values that are not within the electrogram complex. If the electrogram duration is less than about 25% of the pacing cycle length, the median value for all processed signal values is commonly nearly the same as the median value of all non-complex processed signals. In this usual case, the median value for all processed signal values can be used for the threshold. This is the case since in normal tissue, most signals are near the iso-electric line, i.e., the signals are very small. In the above-described method, it is valuable to process the signal values for each heart beat separately, using signal segments from 1 to 1-½ cycle lengths long. Signal segments including more than one complete cycle reduces the probability that the signal segment will begin or end in the middle of an electrogram complex. When relatively short signal segments are used for analysis (e.g. 1 to 1-½ cycle lengths long), sorting the processed signal values in amplitude order, while maintaining pointers to the time location for each signal value, provides a simple means to implement the above-described method for determining electrogram duration. First, choose the median of the entire processed signal segment as the initial threshold. Then, use the time location of the largest signal to begin a forward and backward search in the processed signal for the beginning and end of the complex. If the complex duration is less than ¼ the cycle length, then stop. If the width of the complex is greater than ¼ the cycle length, redefine the threshold as the median of non-complex values and repeat the search. For longer complex durations, this iteration need not be done more than two to three times, since the solution rapidly converges. For each iteration step, the new threshold can be read directly from the original sorted file, since by definition, all values in the complex were above the original value for the threshold. In addition, if the beginning and ending locations were saved, the search for the newly-defined beginning and end of the complex can begin at the saved locations. Each iteration results in an increase or no change in measured electrogram duration. The iteration terminates when no change in duration occurs. Other methods for defining the threshold value to determine the electrogram complex duration can be employed.

Pacing artifacts can significantly complicate the task of automatically determining PPI, especially for electrode pairs close to the pacing sites. This is because the pacing artifacts are temporally close to the beginning of the electrogram complex. There are several ways to overcome the interference of the pacing artifacts and to simplify the task of determining the beginning of each electrogram complex. In some embodiments, signals recorded while pacing signals are applied and for 1 to 2 milliseconds after the termination of pacing signal application are ignored. Since the pacing artifact is propagated electrically, the pacing artifact is synchronous in all recording channels. Therefore, one approach is simply to ignore all signals that are recorded during the pacing. In other embodiments, the effects of pacing artifacts can be reduced or eliminated entirely using either nonlinear or adaptive filtering techniques. These techniques are described in U.S. Pat. No. 5,601,088 which is incorporated in its entirety by reference. In other embodiments, response signals from electrodes located near the electrodes used in pacing are ignored. Since response signals from multiple pacing locations are measured, it is possible to ignore some electrode locations near each pacing site. In other embodiments, response signals from electrodes that are used to apply the pacing signals are ignored. If the electrode is connected to the system for recording during pacing, the input amplifiers are saturated during and for some time after the pacing pulse has terminated. The time to recover from saturation varies by recorder system manufacturer and for different models of recorder systems produced by the same manufacturer. Even for systems with fast recovery from saturation, electrograms recorded from pacing electrodes tend to be greatly distorted for 10 ms to 100 ms after pacing due to after-potentials at the electrode-electrolyte interface following pacing. In further embodiments, the recorder system can be disconnected from all electrodes during the delivery of the pacing signals. For many recorder systems, this would eliminate the pacing artifacts in all recording channels, except for residual artifact signals due to after-potentials which is seen on all channels using the pacing electrode(s).

Figure 5:
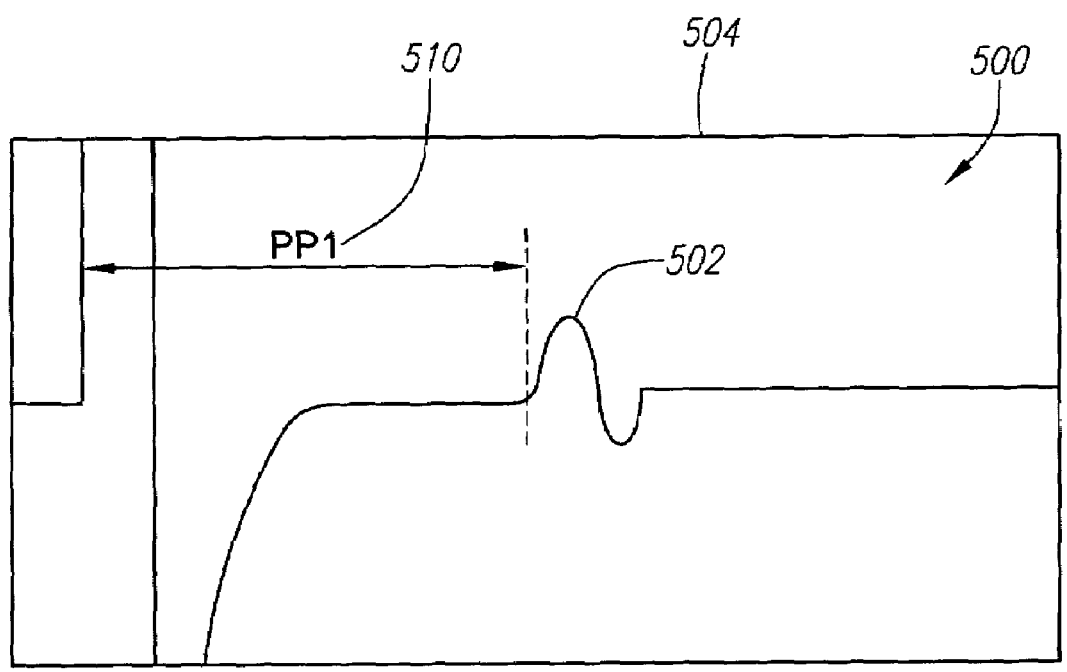
FIG. 5 is an example of an electrogram obtained using the system of FIG. 2.

As discussed previously, applying a dynamic filter can eliminate any baseline shift of a pace channel that could obscure post-pacing signal recovery, while preserving low frequency signal content in a recorded biopotential. FIG. 5 shows an example of an electrogram 500 having data that have been processed by the filtering module 234. The electrogram 500 includes biopotential data 502, which is within a view window 504 presented to a user. As such, the biopotential data 502 is not "lost" as a result of the filtering. FIG. 5 also shows a PPI value 510 that is being automatically determined by the caliper module 236.

In the some embodiments, the signal processor 206 can further include an output interface for presenting information to a user. For example, the signal processor 206 can include a display screen for displaying PPI value(s), or an audio speaker for reporting PPI value(s). Alternatively, instead of an output interface, the signal processor 206 can be coupled to a memory to which PPI value(s) can be stored for later retrieval. In further embodiments, the signal processor 206 can be coupled to an ablation device/system, which controls an ablation process based on signals received from the signal processor 206. For example, when a PPI value indicates that a target ablation site has been located, the ablation device/system then delivers ablation energy to ablate target tissue at the ablation site.

It should be noted that any of the components (e.g., the pace-signal detector 230, the A/D converter 232, the filtering module 234, and the caliper module 236) of the signal processor 206 can be implemented using software, hardware, or a combination of software and hardware. In addition, although the pace-signal detector 230, the A/D converter 232, the filtering module 234, and the caliper module 236 are illustrated as separate components, in other embodiments, one or more of these components can be integrated with another one of these components. For example, in other embodiments, the filtering module 234 and the caliper module 236 can be implemented as a single unit.

Although the signal processor 206 has been described as having filtering and PPI measuring capabilities, in other embodiments, the signal processor 206 can also perform other functions to improve the accuracy of a PPI measurement. In some embodiments, where the heart is stimulated multiple times under the same condition, ensemble averaging is used to improve the effective signal-to-noise ratio. For example, if the heart is paced four times, fiducial points (i.e., identifiable features in a complex that are used as time references) for four complexes from each recording can be aligned and used to ensemble average four beats from each channel, thereby increasing the signal-to-noise level by a factor of two in each channel.

Figure 6A:
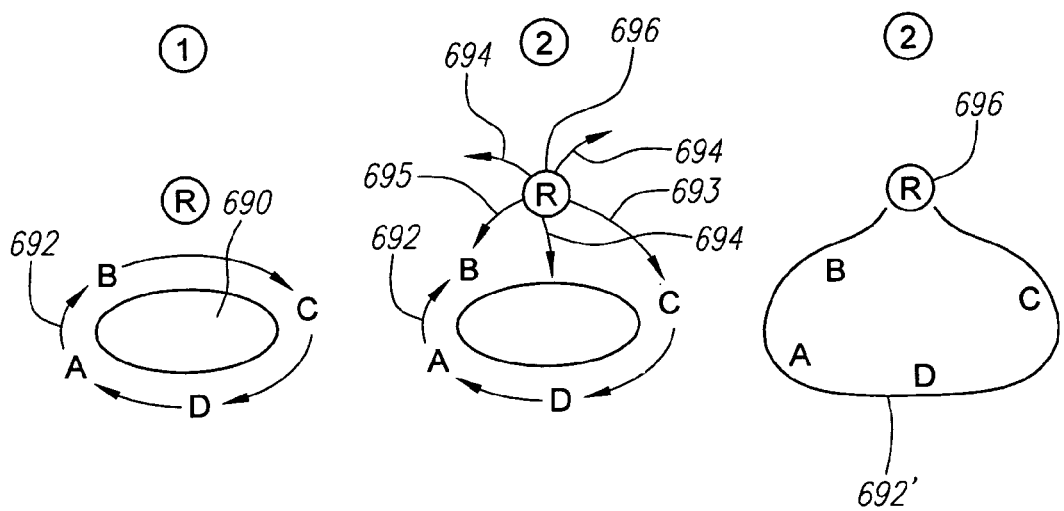
FIG. 6A is a diagram illustrating entrainment pacing at a site remote from a conduction zone.

The above described system 200 and method can significantly improve an entrainment pacing procedure. Entrainment pacing assesses functional participation of a tissue site in the reentrant pathway of a conduction zone. Entrainment involves continuous resetting of the reentrant pathway by stimulating and capturing tissue in the pathway. Tachycardia, or fast beating of the heart, can be entrained in this manner if the tachycardia is caused by a reentrant pathway. FIG. 6A illustrates this concept. Panel 1 shows a hypothetical slow conduction zone 690 and a reentrant pathway 692 around the slow conduction zone 690. Panels 2 and 3 show the effects of a single stimulus at site R. Site R is remote from the reentrant pathway 692. The stimulus captures and excitation waves propagate out in all directions 694 from the stimulus site R 696. The wavefronts 695 traveling from the stimulus site R 696 to site B travels in a direction opposite to the wavefronts in the reentrant pathway 692. These wavefronts 695 from site R 696 are called antidromic wavefronts. Site B is depolarized by the antidromic wavefronts 695. The wavefronts 693 from site R traveling to site C travels in the same direction as the wavefronts in the reentrant pathway 692. The wavefronts 693 traveling to site C are called orthodromic wavefronts. Site C is depolarized by the premature orthodromic wavefronts. An electrogram recorded from this site retains a similar morphology to the electrograms recorded during tachycardia. Panel 3 shows that a new reentrant pathway 692' includes site R 696.

Figure 6B:
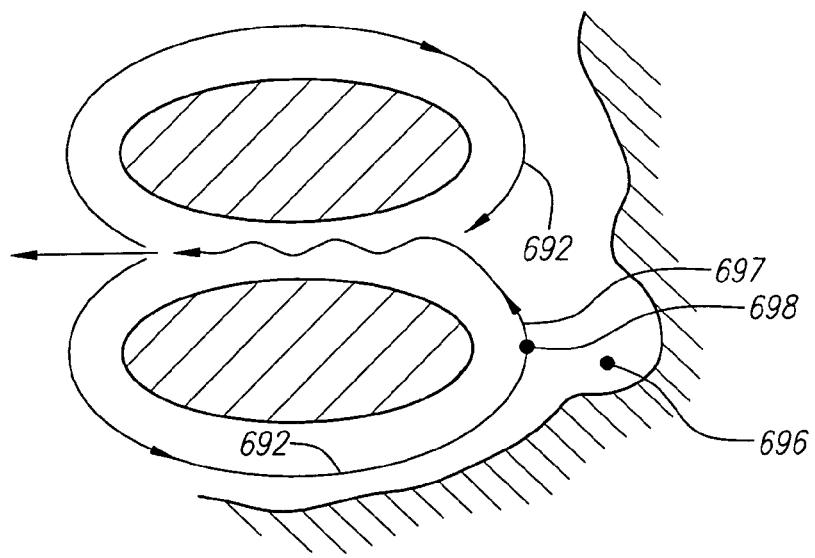
FIG. 6B is a diagram illustrating entrainment pacing at a site within a conduction zone.

The post-pacing interval determined using embodiments of the invention can be analyzed to determine whether a tissue site is near the slow conduction zone or in the reentrant pathway. As discussed previously, the post-pacing interval is the interval from the time when a tissue site is stimulated (e.g., as represented by a detection of a pace signal) to the time when the next nonstimulated depolarization following the stimulus is measured (e.g., as represented by a detection of a biopotential). At the pacing site FIG. 6B shows a two-loop reentrant pathway. Referring to FIG. 6B, if a site 698 in the reentrant pathway 692 is paced, the depolarization following the stimulus is the stimulated orthodromic wavefront 697 after it has propagated through the pathway 692, and returned back to the pacing site 698. This is the revolution time through the pathway 692 and equals the tachycardia cycle length. Referring to FIG. 6B, if a site 696 remote from the reentrant pathway 692 (site R) is paced, the post-pacing interval is the conduction time from the stimulus site 696 to the reentrant pathway 692, through the pathway and back to the pacing site 696. Thus, the post-pacing interval exceeds the tachycardia cycle length when a site outside the reentrant pathway is entrained. A minimum difference between the post-pacing interval and tachycardia cycle length of 30 milliseconds or less is associated with an increased likelihood that the ablation at the site will interrupt the tachycardia. Entrainment pacing is described in "Entrainment Techniques for Mapping Atrial and VTs," Stevenson et al., J Cardiovasc Electrophysiol, Vol. 6, pp. 201-216, March 1995.

Once it is determined that a monitoring electrode is located in a reentrant pathway, the tissue near the monitoring electrode is destroyed by creating a lesion having a prescribed characteristics, e.g., surface area, width, and/or depth.

Computer System Architecture

Figure 7:
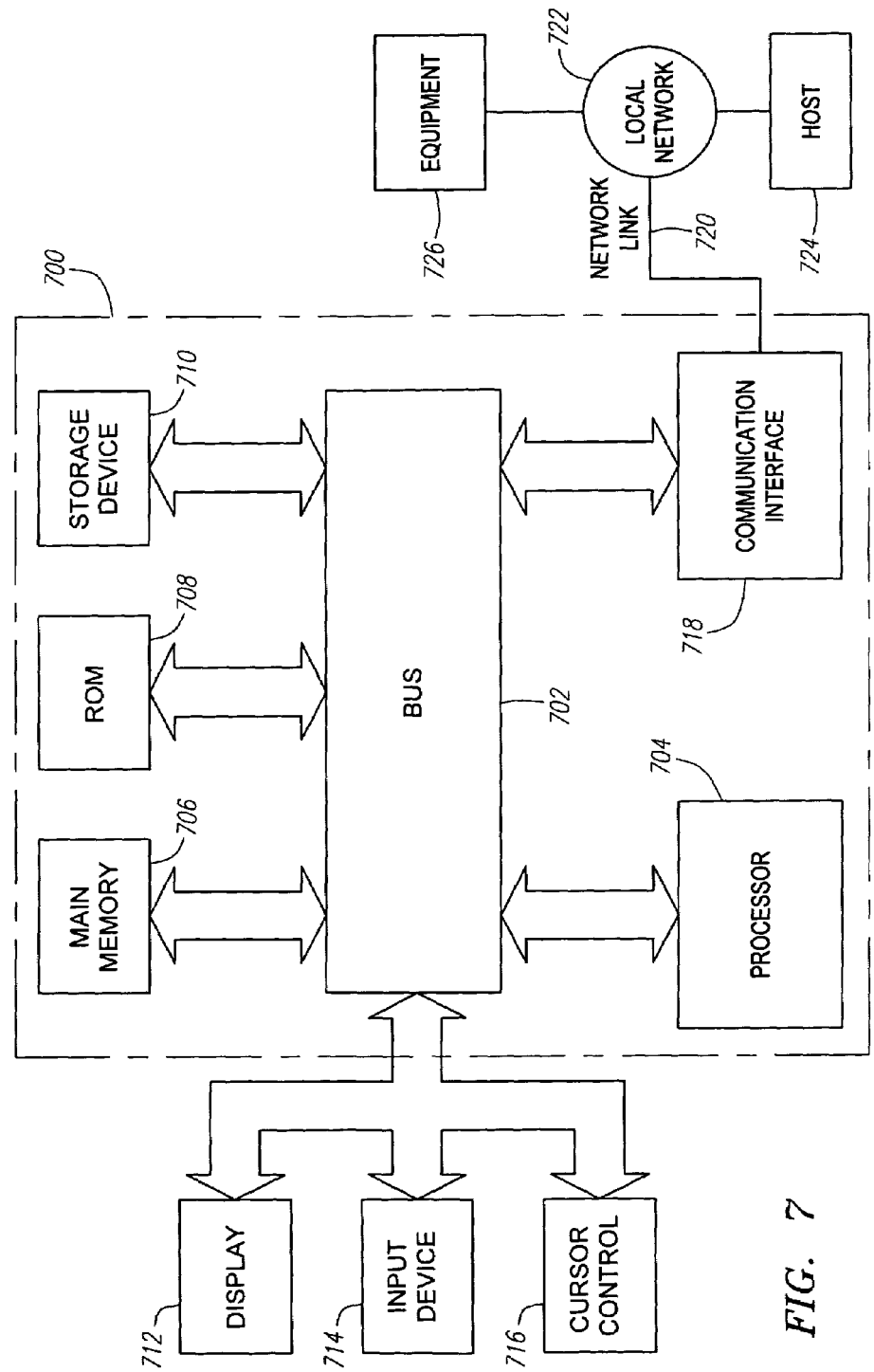
FIG. 7 is a block diagram of a computer hardware system with which embodiments of the present invention can be implemented.

FIG. 7 is a block diagram that illustrates an embodiment of a computer system 700 upon which embodiments of the invention may be implemented. Computer system 700 includes a bus 702 or other communication mechanism for communicating information, and a processor 704 coupled with the bus 702 for processing information. The processor 704 may be configured to perform any of the functions described herein. The computer system 700 also includes a main memory 706, such as a random access memory (RAM) or other dynamic storage device, coupled to the bus 702 for storing information and instructions to be executed by the processor 704. The main memory 706 also may be used for storing temporary variables or other intermediate information during execution of instructions to be executed by the processor 704. The computer system 700 further includes a read only memory (ROM) 708 or other static storage device coupled to the bus 702 for storing static information and instructions for the processor 704. A data storage device 710, such as a magnetic disk or optical disk, is provided and coupled to the bus 702 for storing information and instructions.

The computer system 700 may be coupled via the bus 702 to a display 712, such as a cathode ray tube (CRT), for displaying information, such as biopotential data or electrogram, to a user. An input device 714, including alphanumeric and other keys, is coupled to the bus 702 for communicating information and command selections to processor 704. Another type of user input device is cursor control 716, such as a mouse, a trackball, or cursor direction keys for communicating direction information and command selections to processor 704 and for controlling cursor movement on display 712. This input device typically has two degrees of freedom in two axes, a first axis (e.g., x) and a second axis (e.g., y), that allows the device to specify positions in a plane.

Embodiments of the invention is related to the use of computer system 700 for collecting and processing data. According to one embodiment of the invention, such use is provided by computer system 700 in response to processor 704 executing one or more sequences of one or more instructions contained in the main memory 706. Such instructions may be read into the main memory 706 from another computer-readable medium, such as storage device 710. Execution of the sequences of instructions contained in the main memory 706 causes the processor 704 to perform the process steps described herein. One or more processors in a multi-processing arrangement may also be employed to execute the sequences of instructions contained in the main memory 706. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 704 for execution. Such a medium may take many forms, including but not limited to, non-volatile media, volatile media, and transmission media. Non-volatile media includes, for example, optical or magnetic disks, such as the storage device 710. Volatile media includes dynamic memory, such as the main memory 706. Transmission media includes coaxial cables, copper wire and fiber optics, including the wires that comprise the bus 702. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 704 for execution. For example, the instructions may initially be carried on a magnetic disk of a remote computer. The remote computer can load the instructions into its dynamic memory and send the instructions over a telephone line using a modem. A modem local to the computer system 700 can receive the data on the telephone line and use an infrared transmitter to convert the data to an infrared signal. An infrared detector coupled to the bus 702 can receive the data carried in the infrared signal and place the data on the bus 702. The bus 702 carries the data to the main memory 706, from which the processor 704 retrieves and executes the instructions. The instructions received by the main memory 706 may optionally be stored on the storage device 710 either before or after execution by the processor 704.

The computer system 700 also includes a communication interface 718 coupled to the bus 702. The communication interface 718 provides a two-way data communication coupling to a network link 720 that is connected to a local network 722. For example, the communication interface 718 may be an integrated services digital network (ISDN) card or a modem to provide a data communication connection to a corresponding type of telephone line. As another example, the communication interface 718 may be a local area network (LAN) card to provide a data communication connection to a compatible LAN. Wireless links may also be implemented. In any such implementation, the communication interface 718 sends and receives electrical, electromagnetic or optical signals that carry data streams representing various types of information.

The network link 720 typically provides data communication through one or more networks to other devices. For example, the network link 720 may provide a connection through local network 722 to a host computer 724 or to another equipment 726. The data streams transported over the network link 720 can comprise electrical, electromagnetic or optical signals. The signals through the various networks and the signals on the network link 720 and through the communication interface 718, which carry data to and from the computer system 700, are exemplary forms of carrier waves transporting the information. The computer system 700 can send messages and receive data, including program code, through the network(s), the network link 720, and the communication interface 718.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. For example, in alternative embodiments, instead of using the signal processor 206 to obtain post pacing interval data, the signal processor 206 can be used to automatically obtain other types of data. In addition, an illustrated embodiment needs not have all the aspects or advantages of the invention shown. An aspect or an advantage described in conjunction with a particular embodiment of the present invention is not necessarily limited to that embodiment and can be practiced in any other embodiments of the present invention even if not so illustrated. Thus, the present invention is intended to cover alternatives, modifications, and equivalents that may fall within the spirit and scope of the present invention as defined by the claims.

What is claimed:

1. A system for processing a biopotential signal, comprising:
   a detector for detecting a pacing signal;
   a filtering module for applying a dynamic frequency domain filter to the biopotential signal based on the detected pacing signal; and
   a caliper module for obtaining a post-pacing interval measurement after the dynamic filter is applied.

2. The system of claim 1, wherein the caliper module is configured to measure a duration between the pacing signal and a sensed biopotential.

3. The system of claim 1, wherein the caliper module is for automatically obtaining the post-pacing interval measurement.

4. The system of claim 1, wherein the filtering module is for applying the dynamic filter to the biopotential signal on a pacing channel.

5. The system of claim 1, further comprising a sensor for emitting the pacing signal and for sensing the biopotential signal.

6. The system of claim 1, wherein the detector and filtering module form at least a portion of a tissue mapping system.

7. The system of claim 1, further comprising at least one catheter to which the detector and filtering module are operably coupled.

8. The system of claim 1, wherein the filtering module is for applying the dynamic filter to eliminate pacing artifacts in the biopotential signal, while preserving low frequency content in the biopotential signal.

9. The system of claim 1, wherein the detector is for detecting the pacing signal during a pacing cycle, and the filtering module is for adjusting the dynamic filter during the pacing cycle.

10. The system of claim 1, wherein the dynamic filter is a high frequency filter.

11. The system of claim 10, wherein the filtering module is for adjusting the dynamic filter from a first 3DB point value to a higher second 3DB point value.

12. The system of claim 11, wherein the first 3DB point value is below approximately 50 Hz.

13. The system of claim 11, wherein the second 3DB point value is between approximately 80 Hz and approximately 120 Hz.

14. The system of claim 11, wherein the filtering module is for maintaining the dynamic filter at the second 3DB point value for a predetermined duration.

15. The system of claim 14, wherein the duration is in the range of 10 milliseconds to 100 milliseconds.

16. The system of claim 11, wherein the filter module is for adjusting the dynamic filter from the first 3DB point value to the second 3DB point value upon detection of the pacing signal.

17. The system of claim 10, wherein the filtering module is for toggling the dynamic filter from between a first 3DB point value and a second 3DB point value.

18. A method for processing a biopotential signal, comprising:
  detecting a pacing signal; and
  applying a dynamic frequency domain filter to the biopotential signal based on the detected pacing signal; and
  obtaining a post-pacing interval measurement after the dynamic filter is applied.

19. The method of claim 18, wherein the post-pacing interval measurement is automatically obtained.

20. The method of claim 18, wherein the dynamic filter is applied to the biopotential signal on a pacing channel.

21. The method of claim 18, further comprising mapping tissue based on the obtained post-pacing interval measurement.

22. The method of claim 21, wherein the mapped tissue is cardiac tissue.

23. The method of claim 22, wherein the cardiac tissue mapping comprises entrainment mapping of re-entrant tachycardia.

24. The method of claim 18, wherein the dynamic filter is applied to eliminate pacing artifacts in the biopotential signal, while preserving low frequency content in the biopotential signal.

25. The method of claim 18, wherein the pacing signal is detected during a pacing cycle, and the application of the dynamic filter comprises adjusting the dynamic filter during the pacing cycle.

26. The method of claim 18, wherein the dynamic filter is a high frequency filter.

27. The system of claim 26, wherein the application of the dynamic filter comprises toggling the dynamic filter from between a first 3DB point value and a second 3DB point value.

28. The method of claim 18, wherein the application of the dynamic filter comprises adjusting the dynamic filter from a first 3DB point value to a higher second 3DB point value.

29. The method of claim 28, wherein the first 3DB point value is below approximately 50 Hz.

30. The method of claim 28, wherein the second 3DB point value is between approximately 80 Hz and approximately 120 Hz.

31. The method of claim 28, wherein the dynamic filter is maintained at the second 3DB point value for a predetermined duration.

32. The method of claim 31, wherein the duration is in the range of 10 milliseconds to 100 milliseconds.

33. The method of claim 28, wherein the application of the dynamic filter comprises adjusting the dynamic filter from the first 3DB point value to the second 3DB point value upon detection of the pacing signal.

34. A method for processing a biopotential signal, comprising:
  detecting a pacing signal;
  applying a dynamic frequency domain filter to the biopotential signal based on the detected pacing signal; and
  mapping tissue based on the filtered biopotential signal.

35. The method of claim 34, wherein the tissue mapping comprises obtaining a post-pacing interval measurement after the dynamic filter is applied.

36. The method of claim 34, wherein the dynamic filter is applied to the biopotential signal on a pacing channel.

37. The method of claim 34, wherein the mapped tissue is cardiac tissue.

38. The method of claim 37, wherein the cardiac tissue mapping comprises identifying critical pathways of aberrant intracardiac conduction.

39. The method of claim 38, wherein the aberrant intracardiac conduction is re-entrant tachycardia.

* * * * *